(12) United States Patent
Kunze et al.

(10) Patent No.: US 10,507,143 B2
(45) Date of Patent: Dec. 17, 2019

(54) METHOD AND APPARATUS FOR PREDICTING EXCRETION BY A DIAPER WEARER

(71) Applicant: Reifenhaeuser GmbH & Co. KG Maschinenfabrik, Troisdorf (DE)

(72) Inventors: Bernd Kunze, Hennef (DE); Philipp Pomp, Rheinbach (DE); Thomas Fett, Troisdorf (DE); Andreas Roesner, Bonn (DE)

(73) Assignee: REIFENHAEUSER GMBH & CO. KG MASCHINENFABRIK, Troisdorf (DE)

( * ) Notice: Subject to any disclaimer, the term of this patent is extended or adjusted under 35 U.S.C. 154(b) by 371 days.

(21) Appl. No.: 15/487,758

(22) Filed: Apr. 14, 2017

(65) Prior Publication Data

US 2017/0296397 A1 Oct. 19, 2017

(30) Foreign Application Priority Data

Apr. 15, 2016 (EP) ..................................... 16165643

(51) Int. Cl.
*A61F 13/42* (2006.01)
*G01N 27/04* (2006.01)
*G01P 13/00* (2006.01)
*G08B 31/00* (2006.01)

(52) U.S. Cl.
CPC ........... *A61F 13/42* (2013.01); *G01N 27/048* (2013.01); *G01P 13/00* (2013.01); *G08B 31/00* (2013.01); *A61F 2013/423* (2013.01); *A61F 2013/424* (2013.01); *A61F 2013/425* (2013.01)

(58) Field of Classification Search
CPC ................ A61F 13/42; A61F 2013/423; A61F 2013/424; A61F 2013/425; G01N 27/048; G01P 13/00
USPC ....................................................... 340/573.5
See application file for complete search history.

(56) References Cited

U.S. PATENT DOCUMENTS

| 6,407,308 | B1 | 6/2002 | Roe |
| 7,907,838 | B2 | 3/2011 | Nasiri |
| 8,628,506 | B2 * | 1/2014 | Ales, III ................. A61F 13/42 604/318 |
| 8,821,418 | B2 * | 9/2014 | Meger .................. A61B 5/0002 600/595 |
| 9,119,748 | B2 | 2/2015 | Abraham |
| 9,204,806 | B2 * | 12/2015 | Stivoric ............. G06F 19/3418 |
| 9,675,496 | B1 * | 6/2017 | Alkhamis ............... A61F 13/42 |
| 9,931,251 | B2 * | 4/2018 | Euliano ................. A61F 13/42 |
| 10,238,551 | B2 * | 3/2019 | Wang ...................... A61F 13/42 |

(Continued)

*Primary Examiner* — John A Tweel, Jr.
(74) *Attorney, Agent, or Firm* — Andrew Wilford

(57) ABSTRACT

Excretion by a diaper wearer in a diaper is predicted by providing in or on the diaper on the wearer an excretion detector capable of detecting excretion by the diaper wearer and a motion sensor capable of detecting movements of the diaper wearer. The sensor continuously detects and at least temporarily records movements of the diaper wearer, and these detected movements are analyzed to determine movement patterns. Then, on detection of excretion by the detector, a movement pattern immediately preceding the detection of excretion is stored or flagged as a critical movement pattern. Thereafter each time movements matching the critical movement pattern are detected, a signal is sent to a user.

15 Claims, 2 Drawing Sheets

(56) References Cited

U.S. PATENT DOCUMENTS

2008/0052030 A1  2/2008  Olson
2013/0023786 A1  1/2013  Mani
2018/0333306 A1* 11/2018 Ahong ............... A61B 5/6843

* cited by examiner

METHOD AND APPARATUS FOR PREDICTING EXCRETION BY A DIAPER WEARER

FIELD OF THE INVENTION

The present invention relates to the prediction of excretion by a diaper wearer. More particularly this invention concerns an accessory apparatus and method of predicting such excretions.

BACKGROUND OF THE INVENTION

Diaper accessories as known from U.S. Pat. No. 6,407,308 uses excretion detectors and motion sensors inter alia for producing an early-warning measuring device. Such predictive sensors, also called proactive sensors, can detect posture, pressure, movement, vibration, contraction, tension, blood flow, moisture, temperature, enzymes, bacteria, pH values, conductivity, resistance, capacitance, inductance, and other chemical, biochemical, biological, mechanical, or electrical characteristics. Ultimately, however, only one motion sensor is preferred to detect the muscle contractions of the anal sphincter. Accordingly, the motion sensor must be in the immediate vicinity of the anal sphincter in order to detect its action and thus imminent excretion. It is important to note that such muscle contractions represent a very clear and unambiguous signal. This means that, if a motion sensor is very close to the anal sphincter, the underlying program encounters no noteworthy problems in identifying the contraction pattern. The program must only be capable of detecting a contraction amplitude that is elevated on average. All that is required for this purpose is a preset threshold of the contraction amplitude that lies above the usual range of the basic activity of the anal sphincter.

Nevertheless, this known diaper accessory can only predict solid excretions. However, it is desirable for all excretions, particularly liquid excretions, be able to be predicted so that children can usually be freed from their diaper in time in order to reach the potty. This would accelerate the learning process substantially, thus enabling some children to be potty-trained years earlier. As a result, diaper consumption could be reduced drastically and the environment better protected. Moreover, the precise arrangement of the motion sensor in the immediate vicinity of the anal sphincter is difficult. After all, given the sometimes substantial tendency of small children to move, the motion sensors can easily slip, thus rendering it impossible to detect the muscle contractions.

OBJECTS OF THE INVENTION

It is therefore an object of the present invention to provide an improved method of predicting excretion by a diaper wearer.

Another object is the provision of such an improved method of predicting excretion by a diaper wearer that overcomes the above-given disadvantages, in particular with which excretions—preferably at least liquid excretions—especially of children, can be reliably predicted.

Another object of the invention is to provide a corresponding accessory for carrying out the method.

SUMMARY OF THE INVENTION

Excretion by a diaper wearer in a diaper is predicted according to the invention by providing in or on the diaper on the wearer an excretion detector capable of detecting excretion by the diaper wearer and a motion sensor capable of detecting movements of the diaper wearer. The sensor continuously detects and at least temporarily records movements of the diaper wearer, and these detected movements are analyzed to determine movement patterns. Then, on detection of excretion by the detector, a movement pattern immediately preceding the detection of excretion is stored or flagged as a critical movement pattern. Thereafter each time movements matching the critical movement pattern are detected, a signal is sent to a user.

Furthermore according to the invention, after receiving the signal, the user determines if an excretion event took place in the diaper and, if one did not, deregisters as critical the motion pattern that triggered the signal immediately following the event determined to not have taken place. In addition, if an excretion event did occur, the user confirms as critical the motion pattern that triggered the signal immediately following the event. Furthermore, if the excretion event included solid waste, the user flags or characterizes the motion pattern that triggered the signal immediately following the event as a solid-waste event.

In practice the motion sensor and excretion detector are both connected to a controller that does the pattern determination and keeps track of the patterns found to be critical. This controller may be preloaded with standard patterns or with filters corresponding to known motion patterns of infants so that, right out of the box, an accessory for carrying out the method is likely to work before it is customized for a particular infant.

In other words, the invention teaches a method of predicting excretion by a diaper wearer in a diaper with the aid of a diaper accessory comprising an excretion detector, a motion sensor, and a controller, where the diaper accessory is at least in part on the diaper, the motion sensor detects movement patterns of the diaper wearer, and the controller links the movement patterns with data of the excretion detector with the aid of an excretion detector, such that, when excretions are detected, the movement patterns are stored as critical movement patterns and linked with the excretions detected, preferably afterward, the controller forming the basis for movement-pattern recognition with the aid of the critical movement patterns and learning to differentiate critical from noncritical movement patterns so that the movement patterns are classified with the aid of movement-pattern recognition and some of the movement patterns are determined to be the critical movement patterns, thus enabling predictions to be made regarding imminent excretions, whereby the diaper accessory transmits a prediction signal to warn a user when a prediction is made.

The term "excretion detector" refers particularly to moisture sensors and/or temperature sensors. The controller preferably comprises a processor as well as, also preferably, a memory. The expression "in part on the diaper" means that the diaper accessory can also have two or more parts that are physically separated from one another. For example, only the motion sensor and preferably also a part of the excretion detector is on the diaper, preferably in a housing, whereas the controller can be located not on the diaper but in an external device. It is possible for the excretion and motion sensors to communicate with the controller by radio. According to another preferred embodiment, both a portion of the excretion detector, the motion sensor, and the controller are located in a housing that is on the diaper.

The term "movement pattern" refers particularly to a dataset recorded and further processed by the motion sensor. The dataset preferably includes the profile of a motion amplitude over time. The term "pattern recognition" includes, in particular, feature extraction, feature reduction, and classification. "Feature extraction" refers, for example, to the acquiring of features such as frequencies and amplitude distributions from a movement pattern. "Feature reduction" refers particularly to the restriction of the totality of the features to essential features, with the essential features preferably being especially informative. "Classification" is understood particularly as referring to the correlation of a second movement pattern to a certain class (for example no excretion, liquid excretion, solid excretion) on the basis of the essential features.

The term "prediction signal" is understood as referring to acoustic and/or optical and/or haptic signals, for example. This can be a bright tone, the blinking of an LED, or vibration, for example. Preferably, the prediction signal is forwarded by radio or infrared, for example, to an external device and converted there into an acoustic/optical/haptic signal.

The invention is based on the discovery that infants and small children individually exhibit typical movement patterns shortly before excreting. Children's movement patterns can sometimes vary greatly from case to case. Some children tend to squirm, whereas others kick, for example, or merely remain frozen in a position for a certain time. The range of movement patterns meriting consideration therefore depends first on the individual child and on the type of excretion. It is therefore not possible to make reliable predictions only with the aid of a predefined set of movement patterns. It was found, however, that adaptive movement-pattern recognition is certainly capable of making reliable predictions. The ability to learn is based above all on the measurements of the excretion detector through which predictions that are made with the movement-pattern recognition can be checked. The diaper accessory improves from diaper to diaper, as it were, in terms of the predictions it makes. Successful learning already becomes palpable after a few days, and the diaper accessory completes the learning phase after a few weeks. Excretion is then predicted on a regular basis with high probability. Another substantial advantage of the ability to learn is that the movement patterns of the child can undergo changes over time. But such changes are identified by the diaper accessory within a few days and modified to produce correct predictions again. With consistent use, it is not unusual for children to be potty-trained within the first year of life. For the consumer, this has substantial economic advantages. Moreover, a very large quantity of plastic waste can be saved in this manner.

According to a very preferred embodiment, several of the prediction signals are checked by the user, and the results of these checks are stored by the controller in order to improve the movement-pattern recognition. Preferably, the user check takes precedence over the data of the excretion detector in terms of improving the movement-pattern recognition. For example, a correct or incorrect prediction results in the upgrading or downgrading of the relevance of the movement pattern on which the prediction was based.

It is possible for the diaper accessory to differentiate the data of the excretion detector with respect to the type of excretion. Advantageously, the diaper accessory comprises a moisture sensor and/or a temperature sensor. Preferably, the type of excretion is associated with first, second, and preferably other critical movement patterns. The second movement patterns are advantageously associated with the second and preferably critical movement patterns. It is advantageous if the diaper accessory outputs prediction signals corresponding to the respective type of excretion.

According to a preferred embodiment, the diaper accessory transmits an excretion signal to draw the user's attention when an excretion is detected. The excretion signal or excretion signals include acoustic and/or optical and/or haptic signals, for example. A bright tone or sequence of tones, a blinking LED, or vibration can be considered. Preferably, the excretion signal or excretion signals are transmitted by a communication unit by radio or infrared, for example, to a mobile electronic device where it is converted into an acoustic/haptic signal. It is advantageous for the excretion signal or signals to differ from the prediction signal or prediction signals. The excretion signals advantageously differ from one another, so that the type of excretion is made apparent to the user.

After several of the excretion signals, the user preferably checks whether and preferably which excretion is present, and the results of these checks are stored by the controller for the purpose of improving the excretion-pattern recognition for detecting excretions. This is based on the discovery that adaptive excretion-pattern recognition identifies excretion and the type of excretion more reliably.

It lies within the scope of the invention for the diaper accessory to contain a predefined set of movement patterns and/or excretion patterns. The term "predefined" means in particular that the movement or excretion patterns are stored in the diaper accessory in production or before sale to end customers or as a subsequent update. This can accelerate the learning capacity, since movement patterns and excretion patterns necessary for movement-pattern recognition and excretion-pattern recognition are thus available from the beginning.

It is advantageous if the diaper accessory has a predefined set of filters for improving the differentiation between critical and noncritical movement patterns and/or excretion patterns. In particular, movement patterns that are filtered out are not used for refining the movement-pattern recognition. The filters can filter out extreme movement patterns, for example. It is preferred if the filters set thresholds for motion amplitudes, for example, with motion amplitudes above this threshold having the effect that the associated movement patterns are not used for refining the movement-pattern recognition. It is advantageous if the filters define upper and lower limits for motion amplitudes. In this way, extreme movements are omitted from the outset, so that the child's hops or turns on the changing table are not used for learning in the first place.

According to a very especially preferred embodiment, the data of the excretion detector that are associated with the movement patterns follow the movement patterns over time. Advantageously, the subsequent data of the excretion detector lie within a predetermined time period behind the movement patterns. The time period is one minute, for example.

According to a very preferred embodiment, the diaper accessory comprises a communication unit for communicating with mobile electronic devices. The communication unit is capable of transmitting and receiving radio signals, for example. WLAN, Bluetooth, or GSM radio signals, for example, are worthy of consideration. It is also possible, however, for the communication unit to transmit and receive infrared radiation. The term "communication unit" is understood particularly as referring to an antenna with associated electronics. It lies within the scope of the invention for the diaper accessory to have a timer. The timer is advantageously located in the controller and more preferably near the controller.

The excretion detector is advantageously a moisture sensor. The excretion detector preferably comprises a flat element with a first face of the flat element preferably being longer than a second face. It is advantageous for electrical conductors to be on the flat element, in which case the electrical conductors preferably detect a resistance or capacitance between the electrical conductors. Preferably, at least one of the electrical conductors extends over at least half of the length of the flat element.

It is advantageous if a portion of the excretion detector is mounted reversibly and/or irreversibly on the diaper accessory. Preferably, a portion of the excretion detector, particularly the flat element, is fastened by pressure contacts, for example by a spring clip, to a housing of the diaper accessory. The excretion detector is advantageously embodied such that it can be cleaned hygienically.

According to an especially preferred embodiment, the diaper accessory is fastened reversibly and/or irreversibly to the diaper, for example with a hook-and-loop element and particularly with a Velcro® strip. According to another embodiment, the diaper accessory is fastened to an edge of the diaper by a clip for hanging the diaper accessory.

It is advantageous if the diaper accessory has an operation interface. According to a first embodiment, the operation interface is on the housing and preferably comprises at least one input and/or output element such as, for example, a screen and/or light-emitting diodes and/or knobs. According to another embodiment, the operation interface is on a mobile electronic device and can therefore make use of all of the control elements of the mobile electronic device. Preferably, the diaper accessory comprises an operation interface on the housing and an operation interface on the mobile electronic device.

According to a preferred embodiment, the motion sensor detects twisting and/or straight-line movements. According to an especially preferred embodiment, the motion sensor detects twisting and straight-line movements. The motion sensor can have an acceleration and/or magnetic field sensor and/or a gyroscope. According to a preferred embodiment, the motion sensor is an inertial sensor.

It is possible for the controller to be contained in the parts on the diaper and/or in the parts of the diaper accessory not on the diaper. The controller can be only on the diaper, only on a mobile electronic device, or on both elements at the same time—divided in any manner.

To attain the other object, the invention teaches a diaper accessory for predicting excretion by a diaper wearer in a diaper, particularly a diaper accessory according to the inventive method, with the diaper accessory comprising an excretion detector, a motion sensor, and a controller.

Preferably, the diaper accessory can be at least in parts on the diaper. It is possible for the controller to be embodied such that it, with the aid of the excretion detector, can link movement patterns detected by the motion sensor to data of the excretion detector, in which case the movement patterns are stored as critical movement patterns when excretions are detected and associated with the excretions detected, preferably afterward. The controller is advantageously embodied such that it can form the basis for movement-pattern recognition with the aid of critical movement patterns and can learn to distinguish critical from noncritical movement patterns. Advantageously, the movement patterns can be classified with the aid of movement-pattern recognition such that several of the movement patterns are associated with the critical movement patterns, thus enabling predictions to be made regarding imminent excretions. It is preferred that the diaper accessory be able to transmit a prediction signal to warn a user in the event of a prediction.

BRIEF DESCRIPTION OF THE DRAWING

The above and other objects, features, and advantages will become more readily apparent from the following description, reference being made to the accompanying drawing in which.

SPECIFIC DESCRIPTION OF THE INVENTION

Figure 1:
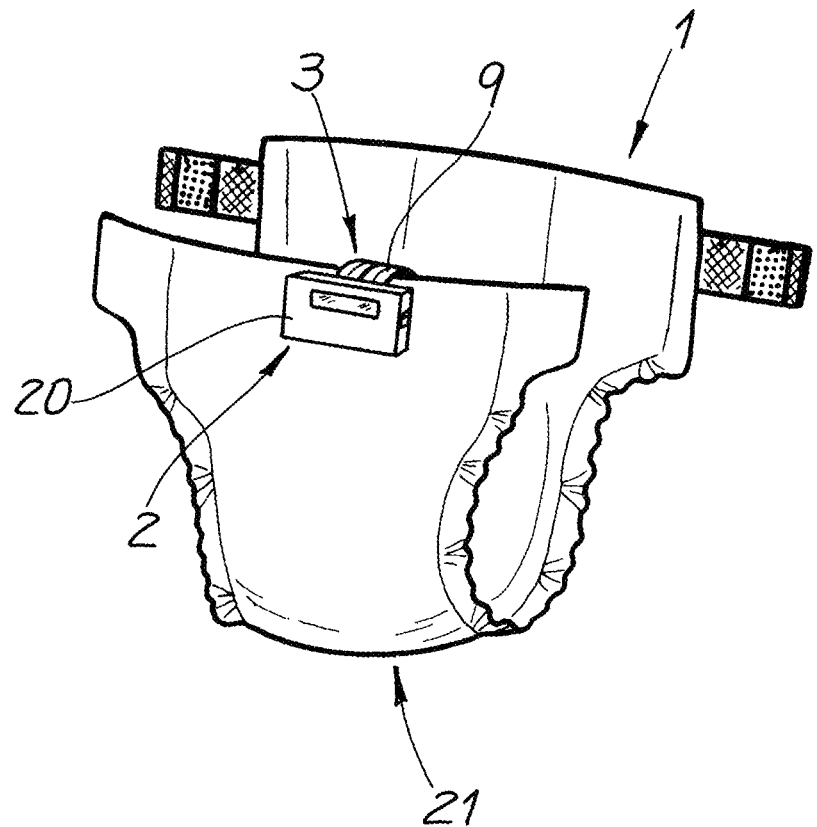
FIG. 1 is a perspective view of a diaper accessory according to the invention mounted on a diaper.

As seen in FIG. 1, a diaper accessory 2 is mounted on a diaper 1 by an unillustrated hook-and-loop fastener. The diaper accessory 2 comprises an excretion detector 3 formed mainly by an absorbent, elongated, and flat element 9. Here, the flat element 9 extends from a housing 20 of the diaper accessory 2 over the upper edge of the diaper 1 and runs from there along the inside of the diaper 1 to a crotch region 21 of the diaper 1. For this purpose, the flat element 9 has an unillustrated hook-and-loop element on one side.

Figure 2:
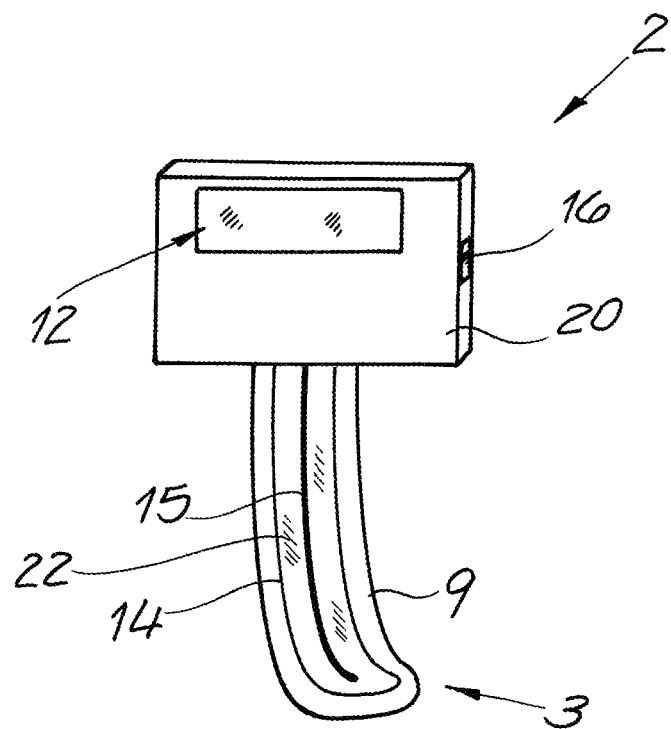
FIG. 2 is a perspective front view of the diaper accessory from FIG. 1.

In FIG. 2, the diaper accessory 2 is shown without the diaper 1. The housing 20 has an on/off switch 16 as well as an interface 12 for operating the diaper accessory 2. The flat element 9 has two electrical conductors 14 and 15, with the conductor 14 surrounding the conductor 15. Here, the excretion detector 3 is a moisture sensor capable of measuring the moisture in the diaper 1 by measurements of a moisture-dependent resistor 22 between the conductors 14 and 15. An increase in moisture in the proximity of the resistor 22 reduces the electrical resistance between the electrical conductors 14 and 15. Consequently, the moisture in the diaper 1 can be assumed to have increased if, when voltage is applied between the electrical conductors 14 and 15, the resistance has dropped.

Figure 3:
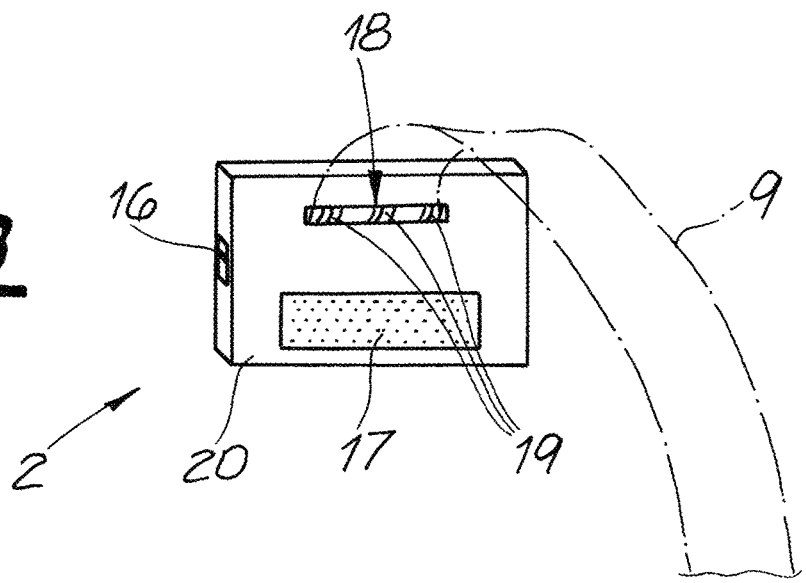
FIG. 3 is a perspective rear view of the diaper accessory from FIGS. 1 and 2.

FIG. 3 is a rear view showing only the housing 20 of the diaper accessory 2. A hook-and-loop strip 17 that provides for a stable hold of the diaper 1 is visible. Moreover, a hole 18 is visible into which an end of the flat element 9 can be pushed. The electrical conductors 14 and 15 of the flat element 9 are connected by pressure contacts 19, preferably spring clips, to the housing 20.

Figure 4:
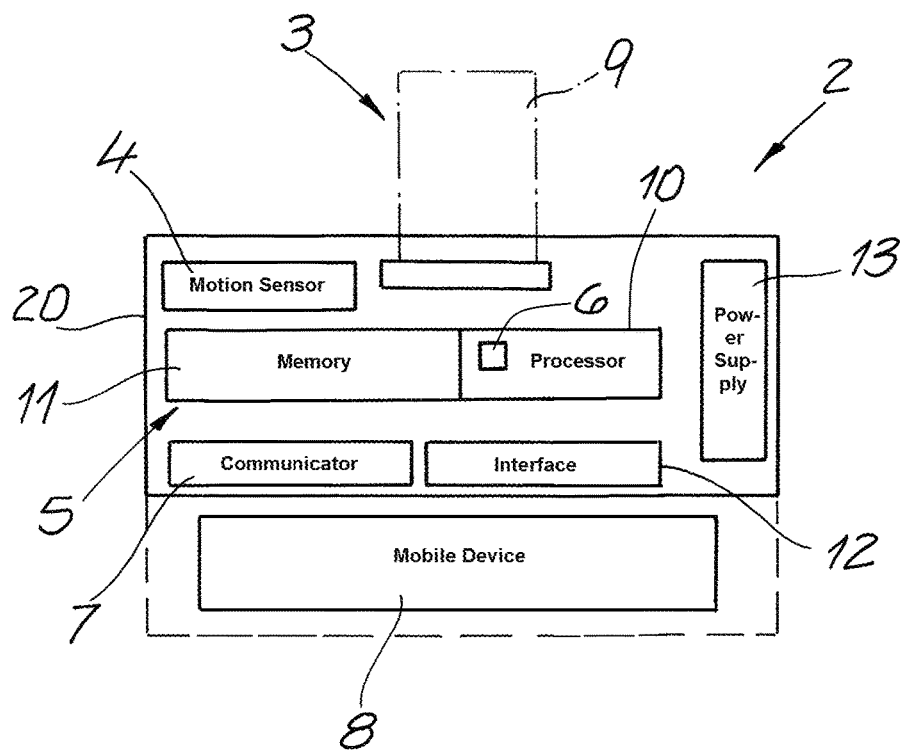
FIG. 4 is a block diagram of the diaper accessory from FIGS. 1 to 3.

In FIG. 4 a block diagram of the diaper accessory 2. In addition to the excretion detector 3 and an operation interface 12, the housing 20 also contains a motion sensor 4, a controller 5, a communication unit 7, and a power supply 13. The motion sensor 4 is an inertial sensor capable of detecting both twisting and straight-line movements. Writhing and kicking movements, which are not unusual before excretions occur, can thus be detected. The controller 5 has a memory 11 and a processor 10 that is provided with a timer 6.

Here, the communication unit 7 is a WLAN interface and can therefore be easily connected to a mobile electronic device 8 such as for example s smart phone or tablet. Here, the diaper accessory 2 also comprises a program on a mobile electronic device 8 in the form of a smart phone as well as the mobile electronic device 8 itself. The program communicates with the controller 5 via a communication unit of the smart phone and the communication unit 7 in the housing 20. Here, the mobile electronic device 8 is therefore a component of the diaper accessory 2 but is not enclosed by the housing 20. This fact is indicated by a broken line.

Upon placement of the diaper 1 onto the diaper wearer, the housing 20 is also fastened by the hook-and-loop strip 17 to the diaper 1 complete with a new inserted flat element 9. The flat element 9 is bent around the upper edge of the diaper 1 and fastened by a respective hook-and-loop element to the inner wall of the diaper 1 down to the crotch region 21. After the diaper 1 is closed and the on/off switch 16 is actuated, the diaper accessory 2 is now ready for use.

The diaper accessory 2 continuously records movement patterns of the diaper wearer with the aid of the motion sensor 4 and the timer 6. As soon as the excretion detector 3 notices a quick drop in the resistance of the electrical resistor 22, the excretion detected in this way is associated with the preceding critical movement pattern. Over time, numerous associations of this kind are established and registered.

Based on the rate of the drop in resistance, the controller 5 can estimate whether it involves sweat or a solid or liquid excretion. Particularly those movement patterns which preceded the solid or liquid excretions are stored and registered as critical movement patterns. These critical movement patterns are used as the basis for movement-pattern recognition. The program for movement-pattern recognition is stored in the memory 11 of the controller 5.

In a feature extraction, various features such as frequencies and amplitude distributions of the movement patterns, for example, are first identified from among the multitude of stored movement patterns from motion/amplitude/time profiles. The most informative features that correlate especially well with the respective excretion type are then selected in a feature reduction.

After a short learning period, the movement-pattern recognition has collected a sufficient number of movement patterns to compile a combination of the most informative features. The movement patterns can now be classified in terms of the type of excretion based on the informative features. For example, if a movement pattern is detected that contains typical features of an imminent liquid excretion, then the controller 5 will transmit a signal via the communication unit 7 to the mobile electronic device 8, thus warning the user of an imminent liquid excretion. The user can then place the diaper wearer, for example a child, on a children's potty. Over time, the child is thus potty-trained very quickly by the diaper 1, thus drastically reducing diaper consumption and protecting the environment accordingly.

Especially in the learning phase, it is advantageous for the user to check after a prediction signal whether an excretion is present and, if so, what kind. The user can then input the result of this check using his mobile electronic device 8, thereby confirming or denying the predictions made by the diaper accessory 2. In case of a confirmation, a movement pattern or a certain feature of the movement pattern is upgraded accordingly, and vice versa. In this way, the ability of the movement-pattern recognition to learn is increased further still.

Moreover, when an excretion is detected in the diaper 1, the diaper accessory 2 advantageously transmits an excretion signal. This excretion signal differs from the prediction signal, so that the user is immediately informed. Furthermore, the user can also confirm or deny the accuracy of the detected type of excretion, so that the diaper accessory 2 is capable of learning with respect to the excretion-pattern recognition as well.

We claim:

1. A method of predicting excretion by a diaper wearer in a diaper, the method comprising the steps of:
    a) providing in or on the diaper on the wearer an excretion detector capable of detecting excretion by the diaper wearer and a motion sensor capable of detecting movements of the diaper wearer;
    b) continuously detecting with the sensor and at least temporarily recording movements of the diaper wearer;
    c) analyzing the detected movements and determining movement patterns therefrom;
    d) on detection of excretion by the detector, registering a movement pattern immediately preceding the detection of excretion as a critical movement pattern; and
    e) thereafter on detecting of movements matching the critical movement pattern, sending a signal to a user.

2. The method defined in claim 1, further comprising the step by the user after step e) of:
    f) determining if an excretion event took place in the diaper and, if one did not, deregistering as critical the motion pattern that triggered the signal immediately following the event determined to not have taken place.

3. The method defined in claim 2, further comprising the step by the user after step e) of:
    g) determining if an excretion event took place in the diaper and, if one did, confirming as critical the motion pattern that triggered the signal immediately following the event.

4. The method defined in claim 1, further comprising the step by the user after step e) of:
    f) determining if an excretion event took place in the diaper and, if one did, whether or not the event included solid waste, and if so, characterizing the motion pattern that triggered the signal immediately following the event as a solid-waste event.

5. The method defined in claim 1, wherein step d) is repeated iteratively to form a library of movement patterns associated with excretion events.

6. The method defined in claim 5, further comprising the step by the user after step e of:
    h) determining if an excretion event took place in the diaper and, if one did, whether or not the event included solid waste, and if so, characterizing the motion pattern that triggered the signal immediately following the event as a solid-waste event.

7. The method defined in claim 1, wherein excretion is detected by detecting moisture in the diaper.

8. The method defined in claim 1, further comprising the step prior to step a) of:
    providing a controller connected to the sensor and to the detector and using the controller to record the movements, determine the patterns, and register the patterns.

9. The method defined in claim 8, wherein the controller is mounted on the diaper.

10. The method defined in claim 8, wherein the controller is in a mobile device linked wirelessly to the sensor and detector.

11. The method defined in claim 8, further comprising the steps of:
    providing the controller prior to first use with a set of predetermined movement patterns; and
    comparing determined movement patterns with the predetermined movement patterns of the set.

12. The method defined in claim 8, further comprising the step of:
providing the controller with a set of filters capable of screening determined motion patterns and aiding in determination of which determined motion patterns are critical and which are not.

13. The method defined in claim 1, further comprising the step of:
sending an excretion signal to the user whenever the excretion detector detects excretion of the wearer of the diaper.

14. The method defined in claim 1, wherein the motion sensor detects straight-line and/or twisting movements of the wearer of the diaper.

15. A diaper accessory for carrying out the method of claim 1, the accessory comprising:
means for releasably securing the motion sensor inside a diaper; and
control means connected to the sensor and detector for recording the movements, determining the patterns, and sending the signal.

\* \* \* \* \*